United States Patent [19]

Clanton et al.

[11] Patent Number: 4,703,887
[45] Date of Patent: Nov. 3, 1987

[54] COLLAPSIBLE PURSE STRING AID FOR USE WITH INTRALUMINAL STAPLING DEVICE

[75] Inventors: Marlene K. Clanton, Somerville, N.J.; Jeffrey Kapec, Westport; Kanuza Tanaka, Cos Cob, both of Conn.

[73] Assignee: Ethicon, Inc., Somerville, N.J.

[21] Appl. No.: 695,812

[22] Filed: Jan. 28, 1985

[51] Int. Cl.⁴ ............................................. A61B 17/04
[52] U.S. Cl. ................................ 227/19; 227/DIG. 1; 128/305; 128/334 R
[58] Field of Search ....................... 227/DIG. 1 T, 19; 128/305, 334 C, 334 R

[56] References Cited

U.S. PATENT DOCUMENTS

| 4,182,339 | 1/1980 | Hardy, Jr. | 128/334 R |
| 4,351,466 | 9/1982 | Noiles | 227/19 X |
| 4,476,863 | 10/1984 | Kanshin | 227/DIG. 1 X |
| 4,592,354 | 6/1986 | Rothfuss | 128/305 |

FOREIGN PATENT DOCUMENTS 0995765  2/1983  U.S.S.R. .......................... 128/334 R

Primary Examiner—Howard N. Goldberg
Assistant Examiner—Taylor J. Ross
Attorney, Agent, or Firm—Robert L. Minier

[57] ABSTRACT

The improvement in an intraluminal stapling instrument comprising a collapsible means disposed on the central member of said instrument. The collapsible means holds the tissue to be joined in the proper position with respect the fasteners being used to accomplish the fastening and also acts as a guide in transecting the vessel.

1 Claim, 8 Drawing Figures

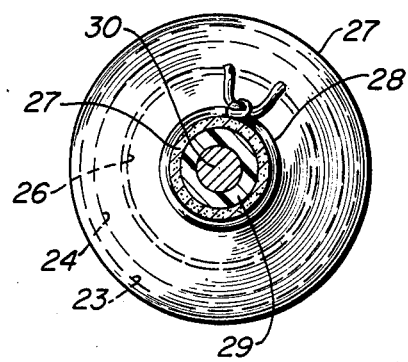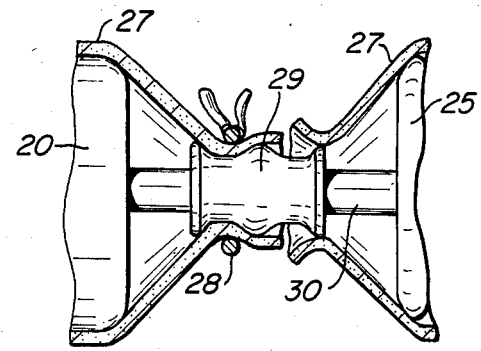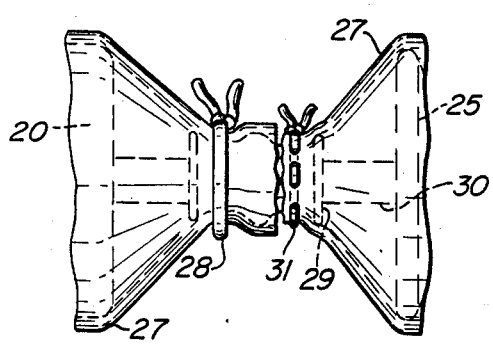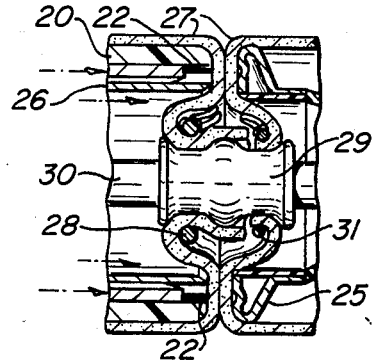

COLLAPSIBLE PURSE STRING AID FOR USE WITH INTRALUMINAL STAPLING DEVICE

The present invention relates to an aid for use with intraluminal stapling devices to assist in the distal purse string placement of the vessel or hollow organ.

BACKGROUND OF THE INVENTION

In recent years there have been developed a number of instruments for placing fasteners in a circular configuration or in a plurality of circular configurations for use in reconnecting severed vessels or hollow organs. These devices are used to perform anastomosis; that is, join the cut end of hollow organs or vessels. Whenever the term "vessel" is used throughout this specification it means a hollow tubular organ; such as intestine, esophagus, blood vessel and the like.

Generally speaking, these intraluminal stapling devices comprise a centrally extending longitudinal member on which there is mounted a circular anvil member and a circular staple holding member. These members are separated from one another but are movable along the centrally located member so that they may be placed adjacent each other. To join a severed vessel, one end of the severed vessel is pulled over the anvil portion of the intraluminal device. A purse string suture; that is, a loosely placed suture, is placed around the cut end of the vessel in a manner to act as a purse string so that it may be pulled tight and pulls the loose end of the vessel down tightly about the centrally located member with portions of the vessel or the tissue then disposed directly underneath the anvil of the instrument. The opposite end of the vessel to be joined is pulled over the stapling portion of the instrument in a similar manner. It is also pulled down utilizing the purse string suture so that it is tied against the centrally located member of the instrument and the tissue underlies the staple applying member. At this point, the staple and anvil are moved towards one another to provide a correct gap between the tissues to be joined. Once that correct gap is obtained, the staples are fired, joining the tissues. Staples may be disposed in various arrays, although usually a pair of concentric circles with the staples offset in adjacent circles is used. Once the staples have been fired, a circular knife, which has a smaller diameter than the smallest array of staples that have been fired, severs the tissue inside the staple line and outside the purse string sutures. The anvil and staple holder may then be backed off or separated and the instrument carefully removed from the rejoined vessel An example of such an instrument is more fully disclosed in U.S. Pat. No. 4,351,466, issued Sept. 28, 1982.

As can be appreciated from the above description, a critical point in the procedure is to be sure the tissue is positioned up against the central longitudinal extending member of the instrument so that the tissue underlies those portions of the instrument which are used to join the tissue together. Depending on the location of the vessel, size of the vessel, etc., it is often very difficult, if not virtually impossible, to place a suitable purse string suture in a manner so as to insure good juxtaposition of the vessels. This is especially true in low colon anastamosis where it may be very difficult to place the purse string suture on the distal end of the vessel.

It is an object of the present invention to provide a simple means for gathering and tying a vessel in a desired location. It is a further object of the present invention to provide a means for easily securing the distal end of a vessel to provide for anastamosis of that vessel. It is a further object of the present invention to provide means which can readily position a vessel to be disected in a desired manner even in the most difficult positions in which to work.

SUMMARY OF THE PRESENT INVENTION

What we have discovered is an improvement to an intraluminal stapling instrument used to join the open ends of vessels. Such an instrument generally comprises a central longitudinally extending member. Disposed on the central longitudinally extending member are a pair of fastening means. At least one of said fastening means is slidably movable toward and away from the other along the central member. One of the fastening means carries fasteners while the other fastening means is an anvil for crimping the fasteners or otherwise securing the fasteners in place once they are set in the vessels to be joined. It is preferred that the anvil fastening means be movable. In use the instrument is placed within the lumen of the vessels to be joined. One of the fastening means carries a circular array of fasteners disposed about the central member. The fasteners are used to join together and hold the joined vessels together. Our improvement comprises collapsible means disposed on the central member and about which the vessel to be disected and rejoined is held in position adjacent the central member. Our collapsible means positions the open end of the disected vessel beneath the circular array of fasteners whereby when the intraluminal stapling device is actuated, the fasteners engage the vessel adjacent the open end of the vessel. In certain embodiments of the present invention, our collapsible means is a resilient member that collapses under pressure. In use, the intraluminal stapling instrument is introduced into the organ. The instrument is opened by moving the means carrying the circular array of fasteners and the securing means away from each other to expose the collapsible means disposed on the central longitudinally extending member. The vessel is tied tightly about the collapsible means using an appropriate ligature. The vessel is transected using the collapsible means as a guide. The diseased section of the vessel is removed. The proximal end of the vessel is then secured about the central member using a purse string suture to cause the vessel to be positioned correctly with respect to the fastener means. The fastener means carrying the circular array of fasteners and the securing means are brought together and the instrument actuated to set the fasteners and join the vessels and cut the tissue between the fasteners and the tied areas.

BRIEF DESCRIPTION OF THE DRAWINGS

The invention will be more fully described in conjunction with the accompanying drawings wherein:

FIG. 3 is a view taken along line 3—3 of FIG. 2 with certain portions of the vessel removed;

FIG. 4 is a cross-sectional view of the instrument of FIG. 2 with the vessel transected;

FIG. 5 is a cross-sectional view of the instrument of FIG. 2 with the vessel disected and the proximal end of the vessel tied about the instrument with a purse string suture;

FIG. 6 is a cross-sectional view of the instrument of FIG. 2 with the vessels joined;

DETAILED DESCRIPTION OF THE DRAWINGS

Figure 1:
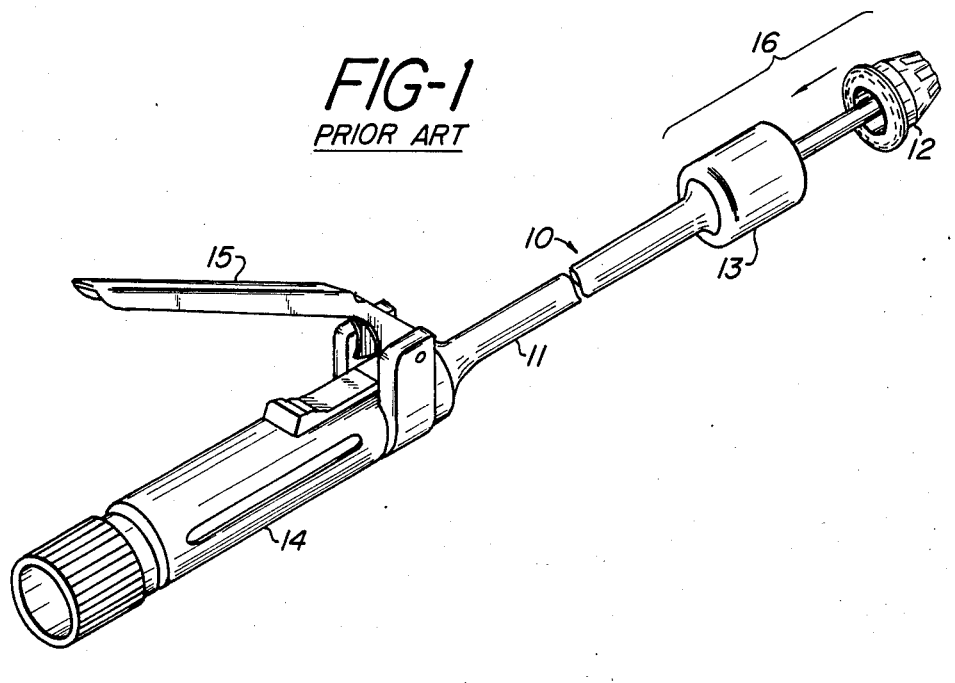
FIG. 1 is a perspective view of one type of intraluminal stapling instrument with which the improvement of the present invention may be used.
Figure 2:
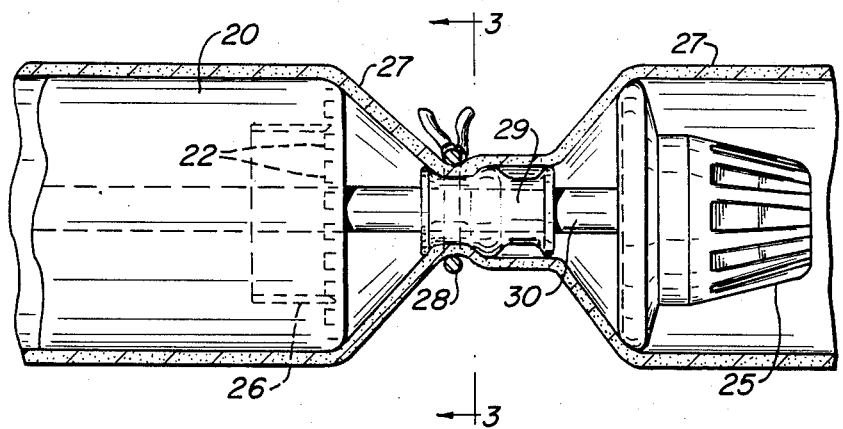
FIG. 2 is a cross-sectional view of an intraluminal stapling instrument depicting the improvement of the present invention with a vessel tied in place.

Referring to the drawings, in FIG. 1 there is shown a perspective view of an intraluminal stapling instrument 10 which may be used with the improvement of the present invention. The intraluminal stapling instrument comprises a centrally disposed longitudinally extending member 11. Disposed at one end of the central member is a movable securing means or anvil 12 and spaced a distance from the anvil is a fastening member 13 carrying suitable tissue fasteners. At the opposite end of the central longitudinally extending member is means 14 for controlling the distance between the slideably movable anvil and the fastening member. Also disposed at the same end is means 15 for firing the fasteners carried by the fastening member. In use, the operating end 16 of the instrument is passed entirely through one end of the vessel to be joined. The other portion of the vessel to be joined is slipped over the anvil and in the prior instruments the vessel tied via a purse string suture down about the centrally extending longitudinal member. In the prior instruments the open end of the vessel through which the instrument is passed is also tied using a purse string suture about the centrally extending longitudinal member and adjacent the fastening member. The knob 14 at the control end of the instrument is turned to bring the fastening member and the anvil to the correct gap for joining tissue. At this point, the firing means 15 is actuated and the fasteners placed in the tissue. A circular knife is actuated to cut the tissue within the circular array of fasteners. At this point, the knob at the control end is backed off slightly to separate the anvil and the fastening member and the instrument gently removed from the reconnected vessel.

As may be more clearly seen in FIGS. 2 through 6, the instrument of the present invention has a fastening member 20. One end of the member 20 carries a plurality of fasteners 22, in this instance, metal fasteners, and these metal fasteners are disposed in two circular arrays 23 and 24 of fasteners with the fasteners offset in the arrays. The anvil 25 is movable on the centrally located member. The fastening member 20 also carries a circular knife 26 which is disposed within the inner circular array of fasteners. The fastening member carries suitable pushers and a suitable actuator (not shown) as is well known in the art for actuating both the fasteners and the knife once the fastening member and the anvil are correctly spaced to join the desired tissue. The instrument is positioned in the vessel 27 to be disected. The vessel is tied with a ligature 28 about the collapsible means 29 on the centrally located member 30. The collapsible means is made from a resilient plastic and has a single corrugation on its surface. As seen in FIG. 4 the vessel is transected adjacent the collapsible means using the collpasible means as a guide and the diseased portion of the vessel removed. As seen in FIG. 5 the proximal end of the disected vessel is tied about the central member 30 using an appropriate ligature 31.

The anvil 25 is moved to the fastening member 20 and the appropriate gap set. As shown in the FIG. 6, the fasteners are placed. The knife may then be actuated to cut the vessel between. The fastening member is backed off and the instrument removed.

Figure 7:
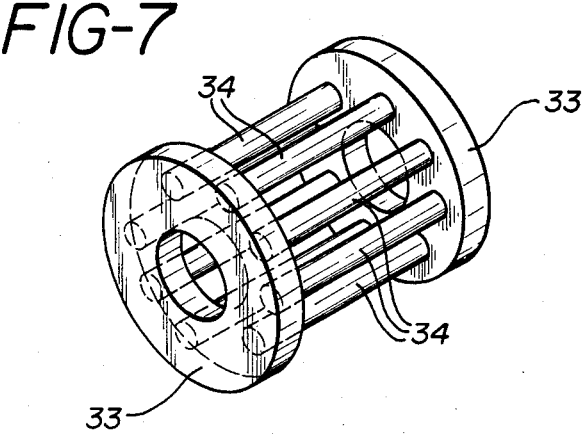
FIG. 7 is a perspective view of one type of collapsible means of the present invention.

The collapsible means may be made from either metal or polymeric material or similar materials as desired. It is preferred that the collapsible means be relatively stationary on the central member or at least not freely movable. In FIG. 7, there is shown another embodiment of the collapsible means of the present invention. In this embodiment, the means comprises a pair of circular discs 33 connected by collapsible stringes 34 of soft metal or plastic. On tying the vessel about the means the stringes break or collapse and the vessel is secured in place.

Figure 8:
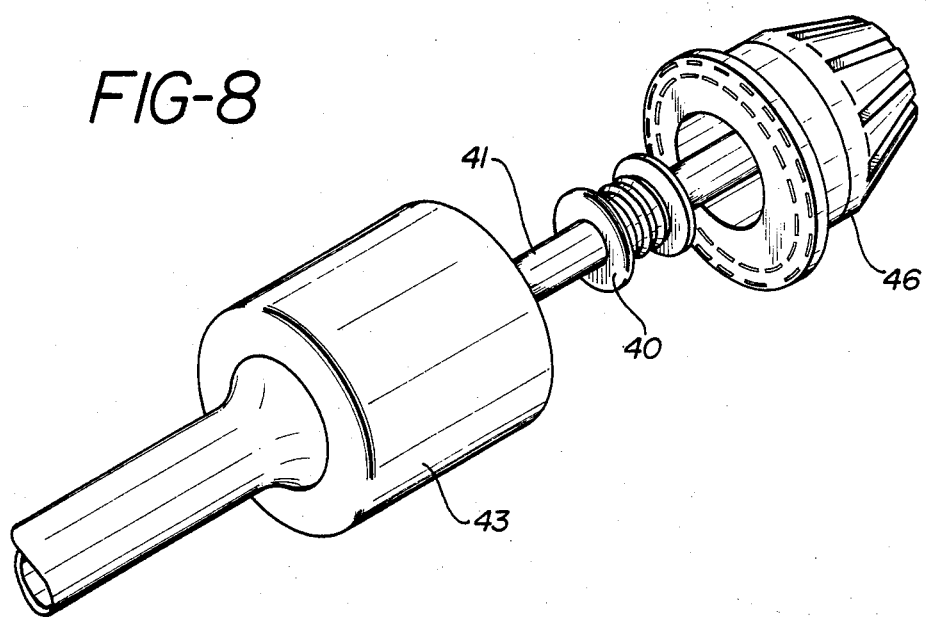
FIG. 8 is an enlarged perspective view of the end portion of an intraluminal stapling instrument showing another type of collapsible means of the present invention positioned on said instrument.

In FIG. 8 there is shown another embodiment of the collapsible means of the present invention. In this embodiment the collapsible means 40 is a collar having an undulating surface disposed on the central longitudinally extending member 41 of an intraluminal stapling instrument. The collapsible means 40 is disposed between the fastening member 43 and the anvil 46 of the instrument. The means is slidably movable along the member 41 and in a preferred embodiment portions of the fastening member 43 and the anvil 46 adjacent the central member 41 are undercut to allow the fastening member to be brought adjacent the anvil to the required tissued gap and the fasteners then fired to join the vessel.

Having now described the invention, it should be readily apparent that many variations and modifications may be made without departing from the spirit and scope of our invention.

What is claimed is:

1. In an intraluminal stapling instrument for joining hollow tubular organs, said instrument including a central longitudinally extending member, means disposed on said member for placement within the lumen of a hollow tubular organ to be joined, said means comprising means for carrying a circular array of fasteners disposed about said central member and means for securing said fasteners after said fasteners have been applied to a hollow tubular organ for joining together and holding the joined organ, said carrying means and said securing means being movable with respect to each other, the improvement comprising:

collapsible means comprising a pair of circular discs connected by a plurality of breakable strings, said means disposed on said central member and positioned between aid carrying means and said securing means whereby a hollow tubular organ may be constricted about said collapsible means adjacent the central member and beneath the circular array of fasteners and the hollow tubular organ transected adjacent said collapsible means using said collapsible means as a guide for transection.

* * * * *